United States Patent

Niznick

[11] Patent Number: 5,989,028
[45] Date of Patent: Nov. 23, 1999

[54] NON-SUBMERGIBLE, ONE-PART, ROOT-FORM ENDOSSEOUS DENTAL IMPLANTS

[75] Inventor: Gerald A. Niznick, Las Vegas, Nev.

[73] Assignee: Core-Vent Corporation, Calabasas Hills, Calif.

[21] Appl. No.: 08/887,463

[22] Filed: Jul. 2, 1997

Related U.S. Application Data

[63] Continuation-in-part of application No. 08/866,705, May 30, 1997, abandoned, which is a continuation-in-part of application No. 08/857,088, May 15, 1997, abandoned.

[51] Int. Cl.⁶ ............................................. A61C 8/00
[52] U.S. Cl. ............................................. 433/173; 433/174
[58] Field of Search ....................................... 433/173, 174

[56] References Cited

U.S. PATENT DOCUMENTS

| | | | |
|---|---|---|---|
| 3,473,222 | 10/1969 | Kester | 433/173 |
| 4,180,910 | 1/1980 | Straumann et al. | 433/173 |
| 4,293,302 | 10/1981 | Hassler et al. | 433/173 |
| 4,324,550 | 4/1982 | Reuther et al. | 433/174 |
| 4,431,416 | 2/1984 | Niznick | 433/174 |
| 4,484,570 | 11/1984 | Sutter et al. | 606/72 |
| 4,854,872 | 8/1989 | Detsch | 433/174 |
| 4,904,187 | 2/1990 | Zingheim | 433/173 |
| 4,960,381 | 10/1990 | Niznick | 433/174 |
| 5,000,686 | 3/1991 | Lazzara et al. | 433/174 |
| 5,015,186 | 5/1991 | Detsch | 433/173 |
| 5,022,860 | 6/1991 | Lazzara et al. | 433/174 |
| 5,125,840 | 6/1992 | Durr et al. | 433/173 |
| 5,169,309 | 12/1992 | Staubli et al. | 433/174 |
| 5,281,140 | 1/1994 | Niznick | 433/172 |
| 5,368,483 | 11/1994 | Sutter et al. | 433/173 |
| 5,435,723 | 7/1995 | O'Brien | 433/174 |
| 5,622,500 | 4/1997 | Niznick | 433/173 |

OTHER PUBLICATIONS

"The Titanium Plasma Spray (TPS) Screw Implant System," Article by Charles A. Babbush, D.D.S., M.Sc.D. and Alan M. Robbins, D.D.S.; published in AO, vol. 80, Scientific 1987.

"Implants Used in Preprosthetic Reconstructive Surgery," from "Reconstructive Preprosthetic Oral and Maxillofacial Surgery," Article by Raymond J. Fonseca, DMD, and W. Howard Davis, DDS, FACD. Published in 1986 by W.B. Saunders Co.

*Primary Examiner*—John J. Wilson
*Attorney, Agent, or Firm*—Patrick F. Bright

[57] ABSTRACT

One-piece, root-form, endosseous dental implants include, in a single implant, a body portion for insertion into an opening in the jawbone of a patient, a neck portion above the body portion, and an abutment portion above the neck portion. The abutment portion includes a peripheral shoulder and an opening into an internally-threaded shaft. The implant may also include internal or external wrench-engaging surfaces.

8 Claims, 13 Drawing Sheets

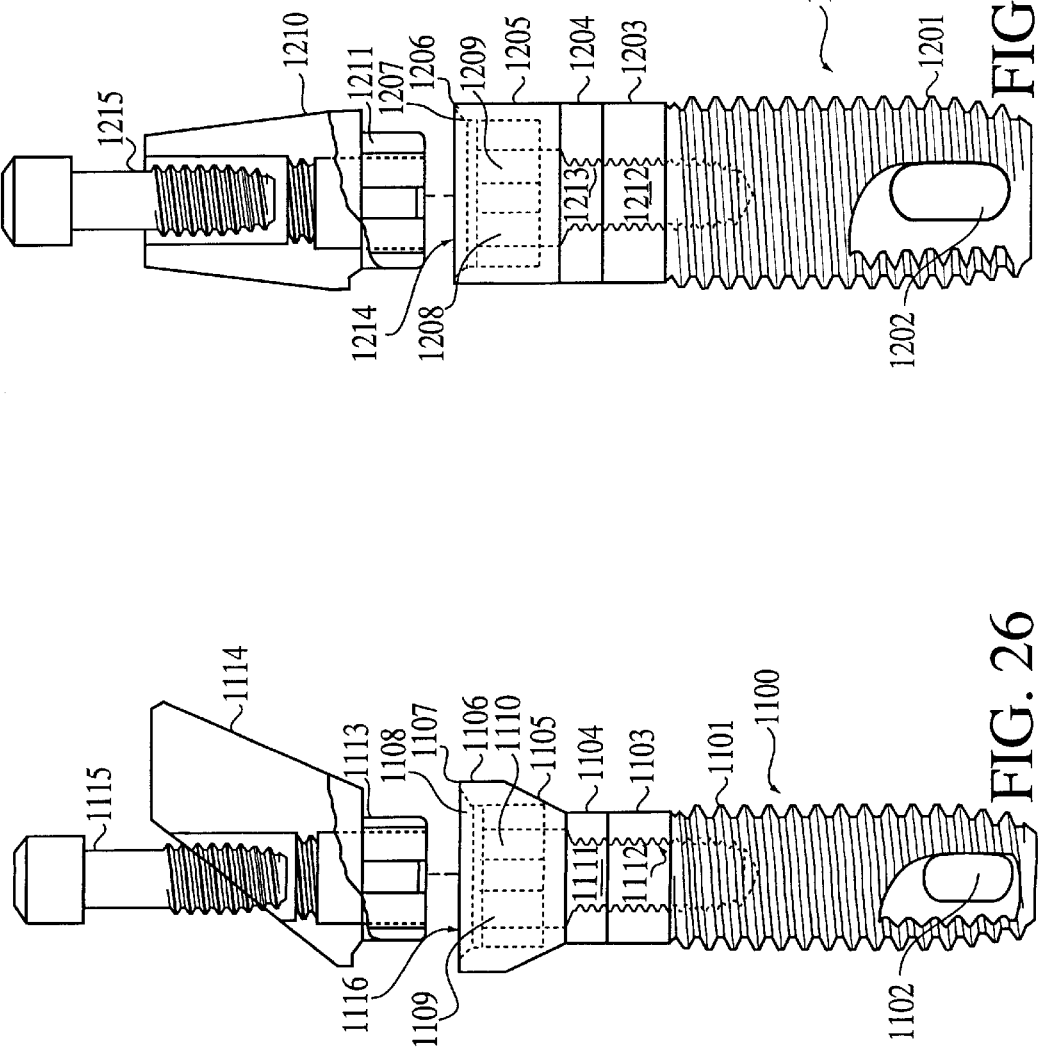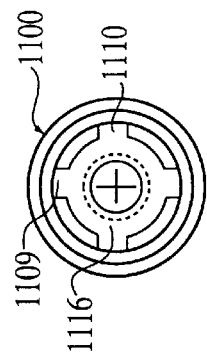

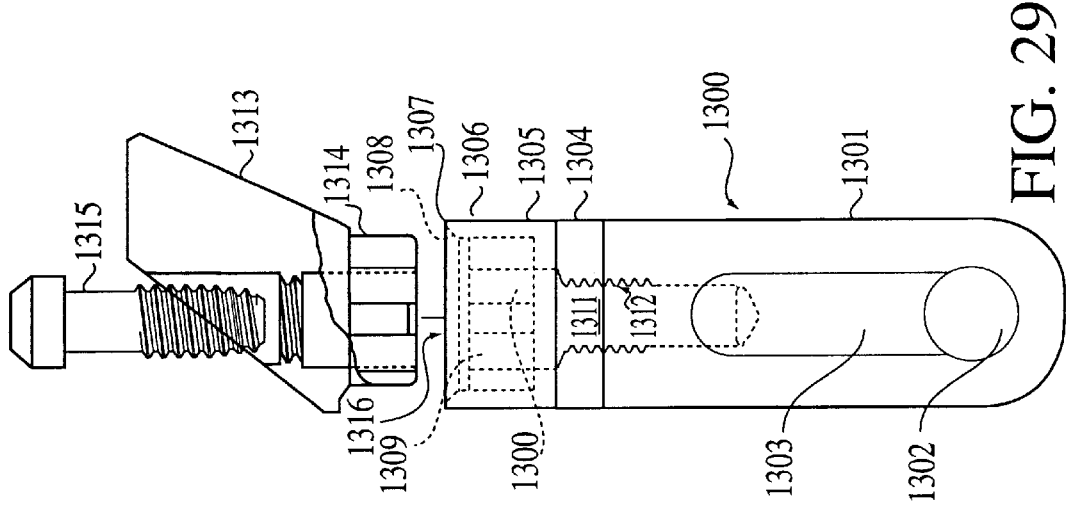

NON-SUBMERGIBLE, ONE-PART, ROOT-FORM ENDOSSEOUS DENTAL IMPLANTS

This application is a continuation-in-part of patent application Ser. No. 08/866,705, filed May 30, 1997, now abandoned which is a continuation in-part application of patent application Ser. No. 08/857,088, filed May 15, 1997, and now abandoned.

This invention relates to non-submerged, root-form, one-part endosseous dental implants. In preferred embodiments, these implants include a body portion for insertion into an opening in the jawbone of a patient; atop the body portion, a neck portion that is sufficiently long to extend through the gum tissue atop such openings, after proper surgical placement in such openings; and an abutment portion atop the neck portion.

The invention also relates to abutment extenders that fit atop the abutment portion of these new dental implants. In some embodiments, these extenders include an end portion with tapered external wall that mates with a complementary, tapered, external wall surface on the abutment portion of the implants. In other embodiments, the extenders include an end portion with a cavity of sufficient size and shape to fit over the abutment portion of the new implants.

The abutment portion has a shape and size adapted to allow connection, as by splinting, of a plurality of such implants placed in nonparallel sites, diverging from one another by up to about 80 degrees, in a common jawbone. Such a connection may, for example, be a screw-retained cast bar, positioned at or above the mucosal tissue for support and retention of an overdenture, or a screw-retained, fixed bridge. These one-part implants provide greater strength than many two-part, endosseous, root form dental implants by eliminating the junction between the implant and a separate abutment.

Root-form endosseous dental implants are adapted to achieve osseointegration, meaning direct attachment to bone, by avoiding overloading the implants during the 3–4 month healing period following surgical placement in jawbone sites. Two-part dental implants require a 2-stage surgical protocol. The first stage comprises inserting an implant, such as the CORE-VENT®, SCREW-VENT®, MICRO-VENT®, BIO-VENT® and BRANEMARK® implants, into the jaw bone, and burying it beneath the mucosal gum tissue for a submerged healing period. The second stage comprises exposing the top of the implant to allow attachment of an abutment. The abutment has a portion that extends above the gum tissue to allow attachment of a prosthesis. Submerged body implants and even non-submerged implants with a body and neck are usually 2-part implants, requiring attachment to the implant of a separate abutment to support a prosthesis.

One method for attaching an abutment to the top of a 2-part implant body (submerged) or neck (non-submerged) is by a threaded connection. An advantage of a 2-part implant is that a variety of abutment designs can be connected to the implant to meet most aesthetic and functional requirements. Abutments of varying diameters and angularity provide many different aesthetic restorations, and allow proper restoration of non-parallel implants placed in a common jawbone, and connected to one another by, for example, a fixed bridge.

Many 2-part implants include, at the top, a wrench-engaging surface, such as an internal or external, multi-sided feature or spline. Such wrench-engaging surfaces may be used for insertion of threaded implants into an opening in a patient's jawbone, or for connection of one-part or multi-part, screw-retained abutments that engage the wrench-engaging surface to provide anti-rotational stability to the abutment. Such a connection provides a stable base for attachment of a cemented single tooth restoration. However, such connections must withstand millions of cycles of loading from chewing every year without loosening, and high shear forces imposed when the connection is placed at an angle to the biting forces without breaking. Sometimes, as a result, these connections weaken and fail.

The 1-stage surgical protocol comprises inserting an implant, e.g., Straumann's ITI® implant, with its cylindrical neck portion extending through the gum tissue at time of implantation, avoiding the need for a second stage of surgery. Such implants may have a neck portion alone that extends through the gum tissue, or, in addition, to the neck portion, a head portion to function as an abutment for support or retention of a prosthesis. An implant that includes body, neck and head portions is referred to as a 1-part implant.

One-part implants avoid the necessity for a second surgical stage, and are not subject to loosening or breaking of the connection between implant and abutment, as in 2-part implants. Advantageously, the 1-part, root-form endosseous dental implants of this invention are simple, strong, and lower in cost than many 2-part implants. Such 1-part implants require less surgical time for placement in a patient's jawbone by eliminating a second surgery, and the time and expense related to attaching a separate abutment to the implant in the second surgery.

In preferred embodiments, the new 1-part, root-form, endosseous dental implants of this invention include a body portion adapted to be inserted into an opening in a patient's jawbone, and to become attached directly to bone at that site through a process called osseointegration. The body portion of these implants may be wholly or partly externally threaded or unthreaded, as in the SCREW-VENT® or BIO-VENT® dental implants; may include a hollow basket structure, as in the CORE-VENT® dental implant; or a ledge-type structure, as in the MICRO-VENT® dental implant. Preferably, the body portion is similar to the body portion of the SCREW-VENT® implant. Preferably, such body portions have externally-threaded surfaces with outside/inside thread diameters of 3.3 mm/2.8 mm, 3.7 mm/3.2 mm, and 4.7 mm/4.2 mm.

Above the threaded body portion of such implants, optionally, is an unthreaded, preferably cylindrical portion with a diameter that is larger than the inside diameter of, and smaller than the outside diameter of the threads of the body portion. Above the body portion of the unthreaded or hollow basket-type implant is an unthreaded, preferably cylindrical portion with a diameter that approximates the diameter of the body portion. Preferably, the length of this unthreaded portion is up to about 2.0 mm. Complementary surgical drills include score lines to aid in placement of this portion at or below the crest of the jawbone at an implant placement site. If mucosal gum tissue is thicker at such sites than normal (e.g. 2–5 mm thick) at the site, some of this unthreaded portion may be placed above the crest of the placement site, thereby adding to the length of the implant's neck portion.

In preferred embodiments, its neck portion is unthreaded, and is up to about 7.0 mm in length. Preferably, the bottom of this neck portion is substantially the same diameter as the unthreaded portion for a length of up to about 2.0 mm. The neck portion of smaller-diameter implants may then widen, or flare outwardly, preferably over a length of up to about 2.0 mm, to a larger-diameter, cylindrical portion, to support and form an abutment portion on the implant's upper surface. In these embodiments, the neck portion has a straight, cylindrical outer wall of about 1.0 mm in length, leading to an outwardly flaring portion of up to about 4.5 mm in diameter. Alternatively, the neck portion may flare outwardly from the top of the body portion directly to the upper surface, or abutment, portion of the implant, or may be substantially straight for its entire length, depending in part on the diameter of the body portion. The overall length of the neck portion may vary from 2.0 mm to about 7.0 mm to accommodate differences in mucosal gum tissue thickness, and permits surgical placement at or above the top of this tissue.

The neck portion of these new 1-part implants is sufficiently long to project through and above mucosal tissue atop an implant placement site in a patient's jawbone. However, the neck portion does not project so far above this tissue that these implants become exposed to biting forces during the surgical healing period.

In preferred embodiments, the abutment portion includes: (1) an internally-threaded shaft that extends downwardly from the top of the abutment portion into the abutment portion and into the neck portion of the implant; (2) a peripheral wall portion that surrounds, and is spaced from, the opening to the internally-threaded shaft; and, optionally, (3) a wrench-engaging surface such as a hex, or a spline, formed on the inner surface of the peripheral wall portion.

For example, in some embodiments, the abutment portion includes: (1) an internally-threaded shaft that extends downwardly from the top of the abutment portion into the abutment portion and into the neck portion of the implant; (2) around the opening to the internally-threaded shaft, external wrench-engaging surface; and (3) a peripheral wall portion that surrounds, and is spaced from, the external wrench-engaging surfaces.

These new implants include an internally-threaded shaft extending downwardly from the top of the implant, and terminating inside the implant. This shaft provides an attachment mechanism for retention of a tissue bar which, in turn, supports and retains a removable overdenture. Alternatively, a fixed bridge may also be retained by screws attached to the internally-threaded shaft.

In preferred embodiments, the abutment portions of these new 1-piece implants provide a substantially level platform to allow splinting or other connection of one such implant to another placed in non-parallel common jawbone sites. Such splinting may, for example, be a screw-retained tissue bar.

In preferred embodiments, the abutment portion of these implants includes, on the inner surface of the peripheral shoulder, a multi-sided, multi-faceted or splined, wrench-engaging surface around the opening to the internally-threaded shaft. These wrench-engaging surfaces function to hold, twist or turn the implant, during insertion into the jawbone site or otherwise, and/or as a connector to implant or abutment extensions. Alternatively, the abutment portion includes external or internal wrench-engaging surfaces within, and around, the opening to the internally-threaded shaft.

The wrench-engaging surfaces, internally-threaded shaft, or both, connect to a one-part or multi-part abutment extension, whether ball-shaped, tapered (straight or angled), to be attached to the abutment portion of these implant. Such extensions may provide anti-rotational support, or retention for cemented restorations or overdentures, thus expanding clinical applications.

External wrench-engaging surfaces may be multi-sided, multi-faceted or splined (as, for example, in Calcitek's endosseous, root-form, external spline or Axel Kirsch's endosseous, root-form, internal spline dental implants) projections adapted to hold, twist or turn the implant for insertion, or for connection to multi-part abutment extensions. Such features are preferably located at, and surround, the opening to the internally-threaded shaft. This multi-sided, wrench-engaging feature, preferably with three to eight, and more preferably six, flat sides, projects upwardly from the base of a trepanned hole formed inside a peripheral shoulder.

This external projection is sufficiently long to provide strength for self-tapping insertion of the implant, where the implant has an externally-threaded body portion, or to provide stability for anti-rotational attachment to an abutment extension, or both. The attachment of such an extension lengthens the 1-part implant to facilitate attachment of certain cemented crowns and bridges or overdentures.

The external projection, in embodiments that include external wrench-engaging facets or sides, is tapered slightly, preferably in the range of about 1 to about 2 degrees, to provide a friction-fit attachment of an extension to the top of the abutment for stable, anti-rotational support of a cemented, single-tooth restoration. See U.S. Pat. No. 5,433,606, incorporated herein by reference, for a description of such tapered projections. Preferably, this projection has a length of about 0.5 mm to about 1.5 mm and a diameter in the range of about 2.0 mm to about 3.0 mm, and more preferably about 2.5 mm.

In preferred embodiments, to splint or otherwise connect, by screw retainer, bar prosthesis or otherwise, the implants of this invention which are surgically placed in non-parallel, common jawbone sites, the abutment portion of these implants includes a peripheral shoulder at the top. In preferred embodiments, the wall of the trepanned hole and the external cylindrical wall of the abutment portion form the shoulder. A coping or other prosthetic connector cylinder may be placed on such a shoulder to form a sealed peripheral region, and is thereupon available to be connected to and provide support for a cast bar. This peripheral shoulder may include a chamfered inner edge, a chamfered outer edge, or both. Preferably, these chamfered edges are at the inner edge, form an angle of up to about 45 degrees with the top surface of the shoulder, and provide some lateral stability without interfering with the passive seating of a bar or other connector that splints or otherwise connects a plurality of such implants in non-parallel, common jawbone sites.

In other embodiments, the peripheral shoulder has a flat top surface that tapers downwardly and outwardly from this top surface onto an outer wall surface. Preferably, the taper angle is in the range of about 5 degrees to about 10 degrees, and most preferably about 8 degrees to about 10 degrees.

Preferably, the external wrench-engaging feature lies within a trepanned hole formed by the shoulder to minimize interference with the passive seating of a cast bar or other connector on a plurality of implants in non-parallel sites in a common jawbone. The external projection may, but need not extend above the shoulder, and preferably extends not more than about 0.5 mm above the shoulder, preferably with an overall length of about 0.5 mm to about 1.5 mm, to provide added strength to the feature. This external projection should not project far enough to interfere with seating a cast bar connector on the shoulders of multiple for implants placed in non-parallel sites in a common jawbone. The degree of divergence between two or more such implants may be reduced from up to about 90 degrees to less than about 70 degrees where an external wrench-engaging surface, if any, projects more than 0.5 mm above a peripheral shoulder atop the implant.

In implant embodiments that include an external wrench-engaging projection at the top of the implant, the projection may be tapered outwardly and downwardly from its upper surface over a length of up to about 0.5 mm. Such tapering facilitates connection of two or more implants in non-parallel, common jawbone sites with up to about 80 degrees of divergence. In addition, the threads in the internally-threaded shaft of such implants preferably begin just below the top of this projection and continue downwardly into the shaft. These threads and the projection, at its preferred height, allow attachment to prosthetic components available for standard hexed abutments sold by Nobelpharma, Implant Innovations, Inc., Core-Vent Corporation and others.

The method of making external wrench-engaging surfaces surrounded by a shoulder atop implants such as those shown in FIGS. 3–6 comprises cutting a notch in the form of a circle atop the implant, and removing the sides of the residual core with the tool shown in FIGS. 7, 8 and 9. This tool comes to a point 100 and has a relief 101 that allows the tool to penetrate into the circular groove to be formed between the external wrench-engaging surfaces and the inner wall of the shoulder, as shown in FIGS. 7 and 8. In preferred embodiments, the diameter of relief 101 is about 0.045 inch; the diameter of the drill face, as shown schematically in FIG. 9, is about 0.117 inch.

In preferred embodiments, the abutment portion may include, around the opening to the internally-threaded shaft, a substantially cylindrical projection without external wrench-engaging surfaces. On the inner surfaces of the peripheral wall portion surrounding, and spaced from, this projection, are wrench-engaging surfaces. Illustrative examples of such implants with externally-threaded body portions are shown in FIGS. 17–19 and with externally-unthreaded body portions in FIGS. 20–22. Each of these implants may be used with abutment extenders, as illustratively shown in FIGS. 17–22.

In other alternative embodiments, as shown illustratively, for example, in FIGS. 11–16, the abutment portion of these implants may include an internally-chamfered wall surface on the shoulder portion. In addition, these implant embodiments may include, below the shoulder portion and within the internally-threaded shaft, internal wrench-engaging surfaces. These internal wrench-engaging surfaces may be multi-sided, multi-faceted or splined (as, for example, in Axel Kirsch's internally-splined, endosseous root-form dental implants) and are adapted to hold, twist or turn the implant for insertion or for connection to multi-part abutment extensions. Such features are preferably located at the opening to the internally-threaded shaft and lie entirely within that shaft. This multi-sided, wrench-engaging feature preferably includes three to eight, and more preferably six, flat sides or splines.

Such implants may have externally-threaded body portions, as shown, for example, in FIGS. 11–13, or externally-unthreaded body portions as shown, for example, in FIGS. 14–16. In addition, the neck portion of these implants may be substantially cylindrical over its entire length, or partly cylindrical and partly flared, as shown, for example, in FIGS. 11 and 14.

The tool shown in FIGS. 7–9 and the method described above for making the implants depicted in FIGS. 3–6, is also useful for forming the shoulder portion and the cylindrical projection within the shoulder portion, as shown, for example, in FIGS. 17–22.

BRIEF DESCRIPTION OF THE DRAWINGS

This invention can better be understood by reference to the drawings which are as follows:

FIGS. 26 and 27 are side elevation views of another embodiment of a root-form, one-part endosseous dental implant having an externally-threaded body portion, a neck portion, and an abutment portion that includes splined wrench-engaging surfaces inside an internally-threaded shaft;

FIG. 28 shows a top plan view of the implant illustrated in FIG. 26;

FIG. 29 shows a side elevation view of another embodiment of a root-form, one-part endosseous dental implant having an externally-unthreaded body portion, a neck portion, and an abutment portion that includes splined, internal wrench-engaging surfaces inside an internally-threaded shaft;

DETAILED DESCRIPTION OF THE PREFERRED EMBODIMENTS

Figure 1:
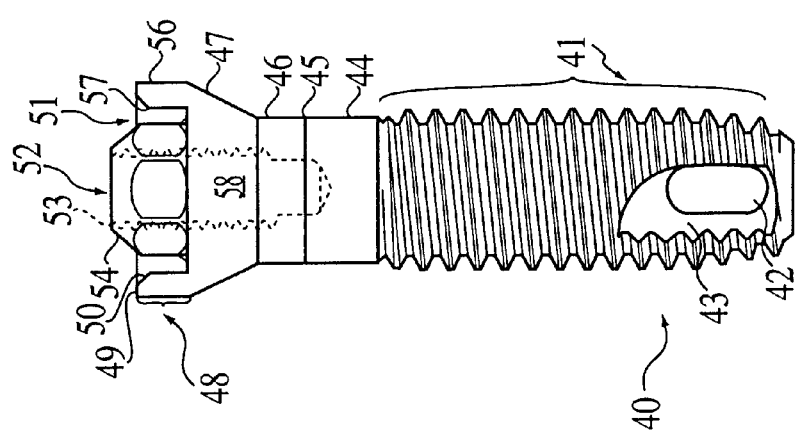
FIG. 1 is a side elevation view of another embodiment of a root-form, one-part endosseous, root-form dental implant having an externally-threaded body portion, a neck portion, and an abutment portion, that includes a peripheral shoulder and, inside said shoulder, upwardly-extending, external wrench-engaging surfaces surrounding an internally-threaded shaft.

FIG. 1 shows 1-part, root-form endosseous dental implant 40 including externally-threaded body portion 41 having, near its distal end, through hole 42 and notch 43 to facilitate self-tapping of implant 40 into an opening formed in a patient's jawbone. Above body portion 41 are cylindrical, unthreaded portion 44, cylindrical, unthreaded, neck portion 46, and outwardly-tapering neck portion 47. Score line 45 separates portion 44 from neck portion 46. Portions 44 and 46 are both cylindrical-shaped, externally-unthreaded, and of substantially the same diameter as the internal diameter of externally-threaded body portion 41.

Above neck portion 47 is abutment portion 48 including cylindrical wall 56. Cylindrical wall 56 includes upper surface 49. At the inside edge of upper surface 49 is chamfer 50. Chamfer 50 tapers inwardly and downwardly at an angle of about 45 degrees from upper surface 49. Below chamfer 50 is internal wall 57. Internal wall 57, chamfer 50, upper surface 49 and cylindrical wall 56 form a peripheral shoulder that surrounds external, multi-sided projection 52.

Projection 52 has six contiguous flats, e.g. flat 55, that lie within the peripheral shoulder. Projection 52 includes substantially flat upper surface 53 and tapered surfaces 54 extending downwardly and outwardly from surface 53. Opening 55 at the center of projection 52 leads into internally-threaded passage 58 which has internal threads 59. Internal threads 59 extend from just below opening 52 a substantial distance into the interior of the body of the implant, and terminate above the end of passage 58.

Figure 2:
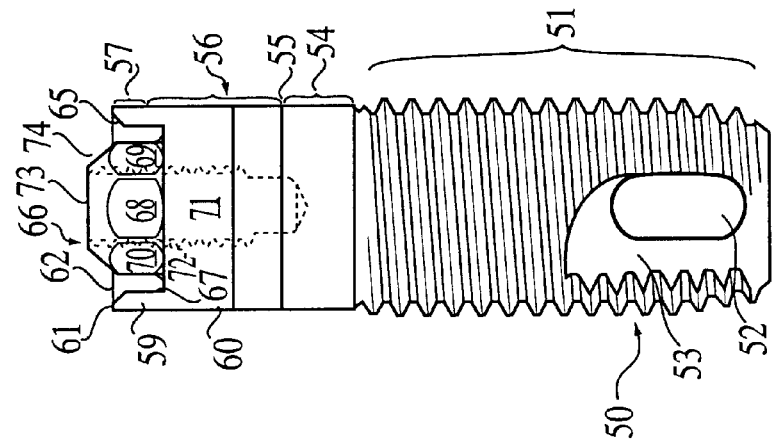
FIG. 2 is a side elevation view of another embodiment of a root-form, one-part endosseous dental implant having an externally-threaded body portion, a neck portion, and an abutment portion that includes external wrench-engaging surfaces in a trepanned hole surrounded by a peripheral shoulder atop the abutment portion of the implant.

FIG. 2 shows one-part, root-form, endosseous dental implant 50 having externally-threaded body portion 51. Near the distal end of body portion 51 are through hole 52 and notch 53. Notch 53 facilitates self-tapping insertion of implant 50 into an opening formed in a patient's jawbone. Above externally-threaded body portion 51 are cylindrical portion 54, score line 55, neck portion 56, and abutment portion 57. Portion 54, neck portion 56, and abutment portion 57 are all substantially cylindrical in shape, externally-unthreaded, and of substantially the same diameter. Abutment portion 57 includes peripheral shoulder 59 formed by external wall 60, upper surface 61, chamfer 62, and internal wall surface 65. Connected to surface 67 within shoulder 59 is external projection 66. Projection 66 has six flat sides such as sides 68/69/70. These multi-sided, wrench-engaging surfaces surround the opening into internally-threaded passage 71. Passage 71 includes internal threads 72. Internal threads 72 extend from just below upper edge 73 of wrench-engaging surfaces 68/69/70 a substantial distance into internal passage 71 which terminates within implant 50 above externally-threaded body portion 51. External projection 66 extends approximately 0.5 mm above surface 61 to flat upper surface 73.

Figure 3:
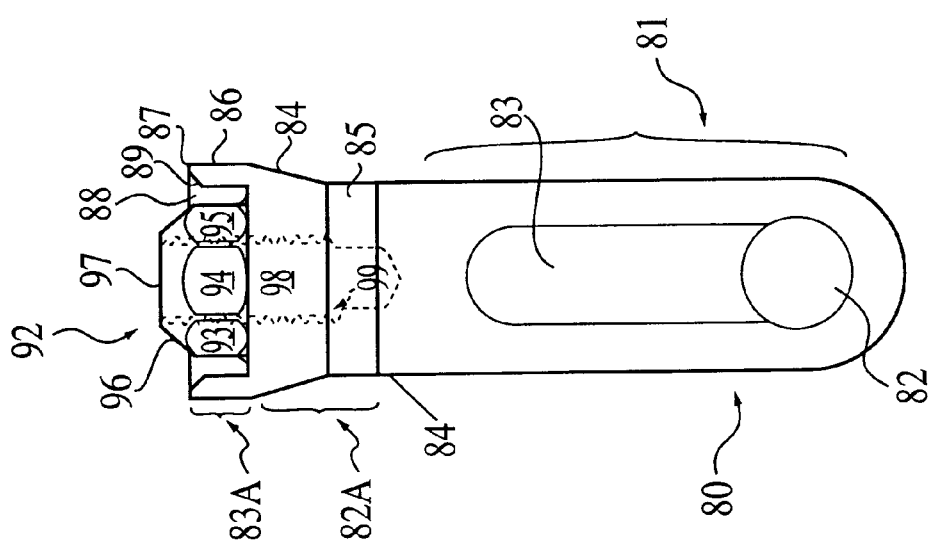
FIG. 3 is a side elevation view of another embodiment of a root-form, one-part endosseous dental implant having an externally-unthreaded body portion, and neck and abutment portions substantially the same as the neck and abutment portions of the implant shown in FIG. 1.
Figure 7:
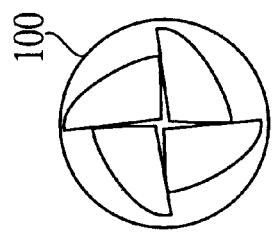
FIGS. 5–7 show devices and methods for forming external wrench-engaging surfaces and a shoulder atop the implants shown in FIGS. 1–4.
Figure 6:
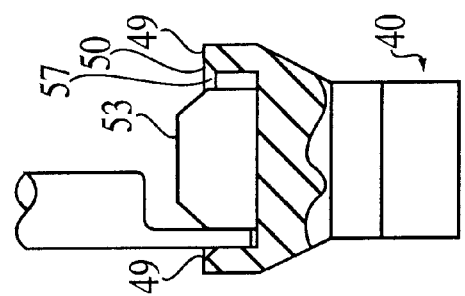

FIG. 3 shows 1-part, root-form endosseous dental implant 80 having body portion 81. Body portion 81 includes, near its distal end, through hole 82. Extending longitudinally along the unthreaded external surface of body portion 81 is longitudinal groove 83 which terminates at the distal end of body portion 81 at through hole 82. Above body portion 81 are neck portion 82A and abutment portion 83A. Score line 84 separates neck portion 82A from body portion 81. Neck portion 82A includes cylindrical portion 85, and outwardly-tapering portion 84. Abutment portion 83A includes cylindrical surface 86, and substantially flat, tapering upper surface 87. Internal wall surface 88, upper surface 87, internally-chamfered region 89 and external wall surface 86 form peripheral shoulder 90 that surrounds trepanned hole 91.

In trepanned hole 91 is external wrench-engaging surface 92 that includes a plurality of six flats 93/94/95. Above these flats are tapered surface 96 and upper surface 97. Upper surface 97 surrounds the opening into internally-threaded shaft 98 that includes internal threads 99 beginning just below opening 97 and continuing downwardly a substantial distance into internally-threaded shaft 98.

Figure 4:
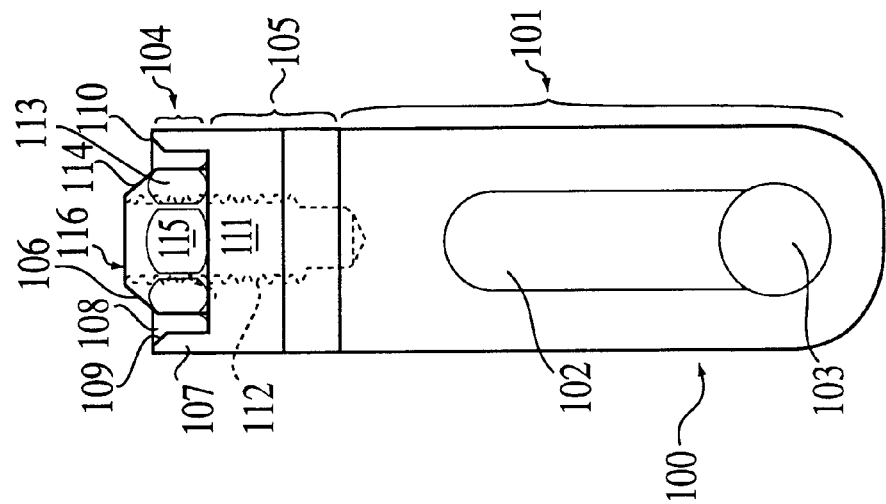
FIG. 4 is a side elevation view of another embodiment of a root-form, one-part endosseous dental implant having an externally-unthreaded body portion and neck and abutment portions substantially the same as the neck and abutment portions of the implant shown in FIG. 2.
Figure 5:
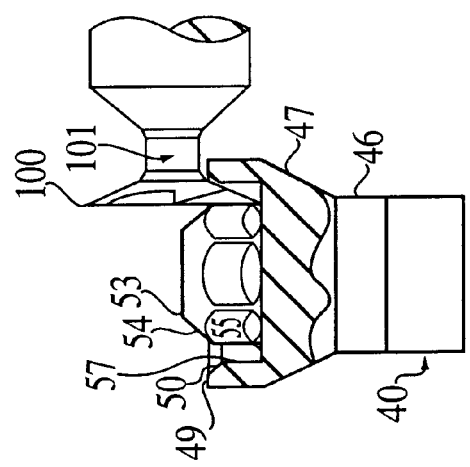

FIG. 4 shows one-part, root-form, endosseous dental implant 100 having unthreaded external body portion 101 with longitudinal groove 102 formed in body portion 101. Groove 102 ends at through hole 103 formed in body portion 101 near the distal end of implant 100. Above body portion 101 is neck portion 105. Above neck portion 105 is abutment portion 104. Abutment portion 104 includes upwardly-projecting, wrench-engaging projection 106 that includes the same features as projection 92 in FIG. 5.

Peripheral shoulder 107 surrounds trepanned hole 108. Shoulder 107 includes chamfer 109 formed at an angle of about 45 degrees with respect to upper surface 110 of implant 100.

Internally-threaded shaft 111 includes internal threads 112 that begin near opening 116 that extend downwardly a substantial distance inside implant 100. Wrench-engaging feature 106 includes six flat, contiguous surfaces, such as flat surfaces 115/113, and upwardly, inwardly-tapering surface 114. Projection 113 extends approximately 0.5 mm above top surface 110 of shoulder 107, permitting implant 100, and the implants shown in FIGS. 1–3, to be connected to one another by a connector, even where the implants are placed in a common jawbone in non-parallel sites that diverge from one another up to about 90 degrees.

Figure 8:
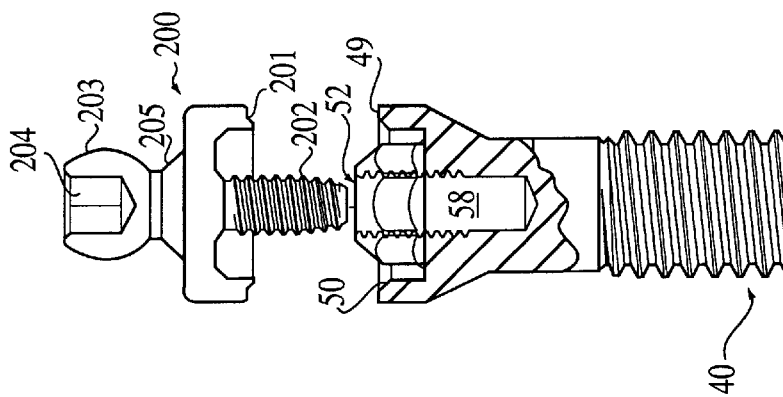

FIG. 8 shows implant 40 used with abutment extender 200. Extender 200 includes threaded shank 202 which is screwed into internally-threaded shaft 58 until lower, chamfered, annular-shaped surface 201 seats on upper surface 49. Extender 200 includes tapered transitional portion 205 and ball joint 203 with internal, multi-sided, wrench-engaging surface 204.

Figure 9:
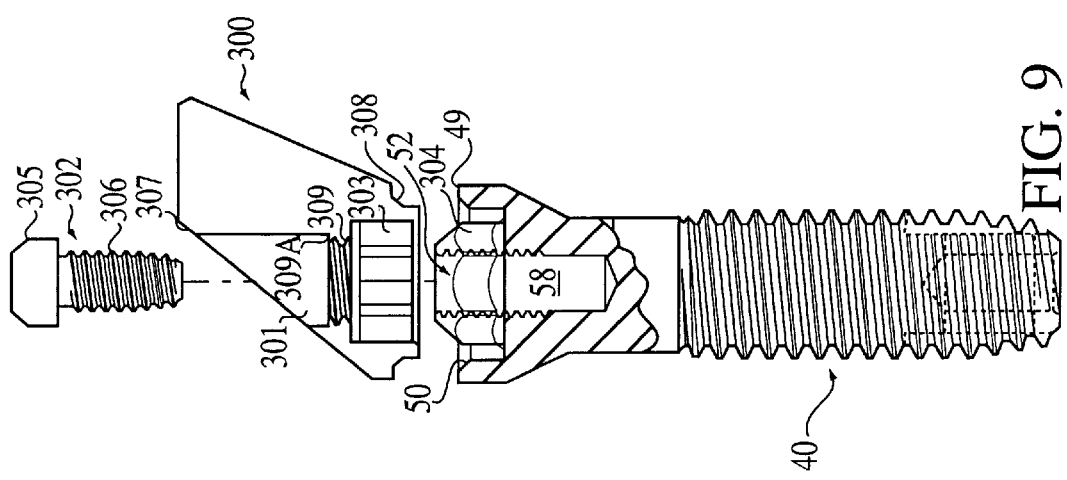

FIG. 9 shows implant 40 used with angled, tapered, abutment extender 300. Extender 300 includes annular, inwardly-chamfered bottom surface 38 that seats on and forms a sealing engagement with upper surface 39. With surface 38 seated on upper surface 49, internal wrench-engaging surfaces 303 engage the flats, such as flat 304, of external projection 52. Extender 300 includes tapered angle surface 307 and opening 301. Screw 302 passes through opening 301, engages threads 309 and internal threads 58 of implant 40. Head 305 of screw 302 seats on surface 309, and functions to hold extender 300 onto implant 40.

Figure 10:
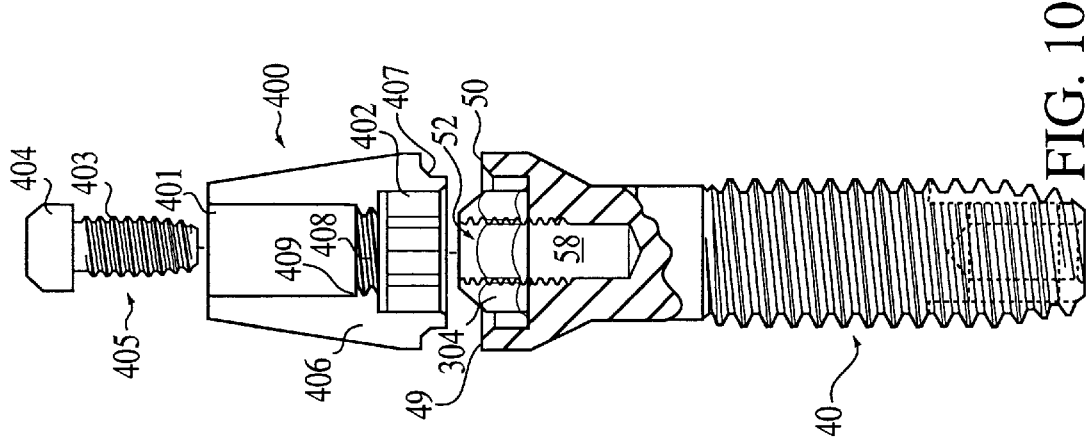
FIGS. 8–10 show the root-form, one-part endosseous dental implant of FIG. 1 used with abutment extenders.

FIG. 10 shows implant 40 used with abutment extender 400. Extender 400 includes lower, annular, internally-chamfered surface 407 that seats on and forms a sealing engagement with upper surface 49. When lower surface 407 is seated on upper surface 49, internal wrench-engaging surfaces 402 engage flats such as flat 304 of projection 52 on implant 40. With extender 400 seated on implant 40, screw 405 is inserted through opening 401, and screws into threads 408 of extender 400 and into internal threads 58 of implant 40. Head 404 of screw 405 thereupon engages upper surface 409 inside extender 400 to hold extender 400 onto implant 40. External tapered surface 406 is used for connection to dental prostheses and other dental connectors.

Figure 12:
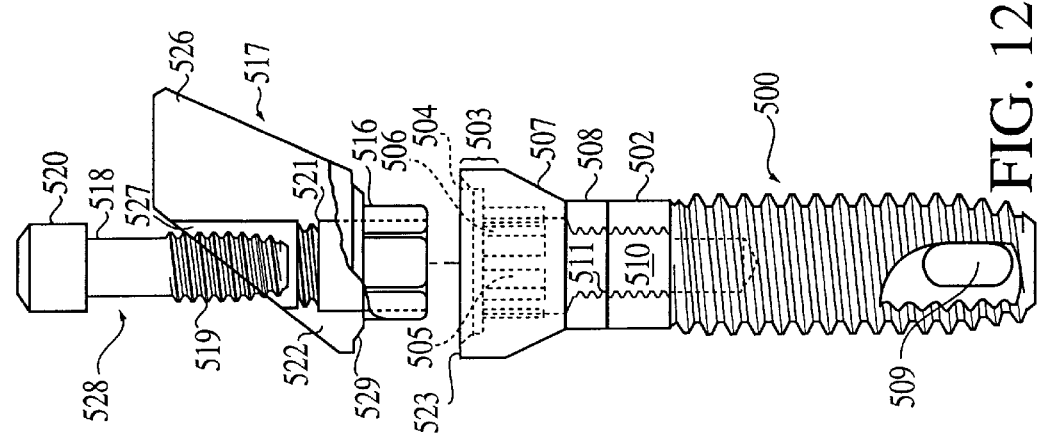
Figure 11:
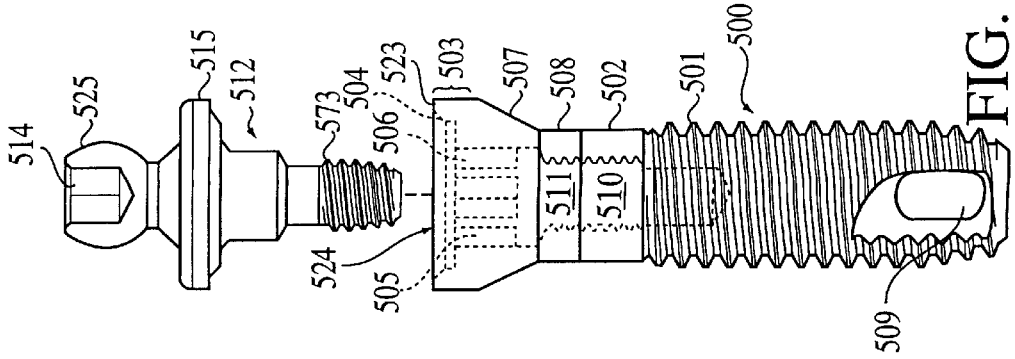

FIGS. 11 and 12 show root-form, one-part endosseous dental implant 500 including externally-threaded body portion 501, unthreaded, substantially cylindrical neck portion 502/508, outwardly-flared neck portion 507, and abutment portion 503. Abutment portion 503 includes a shoulder portion having flat upper surface 523 contiguous with downwardly, internally-extending, chamfered region 504. The shoulder portion surrounds opening 524 into internally-threaded shaft 510 that includes internal threads 511 and multi-sided, wrench-engaging surfaces such as surfaces 505/506. Through-hole 509 includes self-tapping threads to facilitate placement of this implant in a jawbone site.

Above implant 500 in FIG. 11 is one-piece abutment extender 512. Extender 512 includes threaded shank 513, integrally-formed seating portion 515 that seats sealingly on surface 523, and upwardly-projecting, integrally-formed ball connector 525 with internal multi-sided, wrench-engaging surfaces 514.

In FIG. 12, implant 500 is shown for use with two-part abutment 517 including angled extender part 526 with integrally-formed, multi-sided projection 516 that fits into internal, wrench-engaging surfaces 508/506. Extender part 526 includes internal, longitudinally-extending passage 527 having internal threads 522. Bolt member 528 fits into passage 527 with internal threads 519 passing through threads 522 and engaging threads 511 in internally-threaded shaft 510 of implant 500. Cap portion 520 engages surface 521 to hold abutment extender part 526 firmly in place atop implant 500. Extender part 526 includes chamfered surface 529 that sealingly seats on chamfered surface 504.

Figure 13:
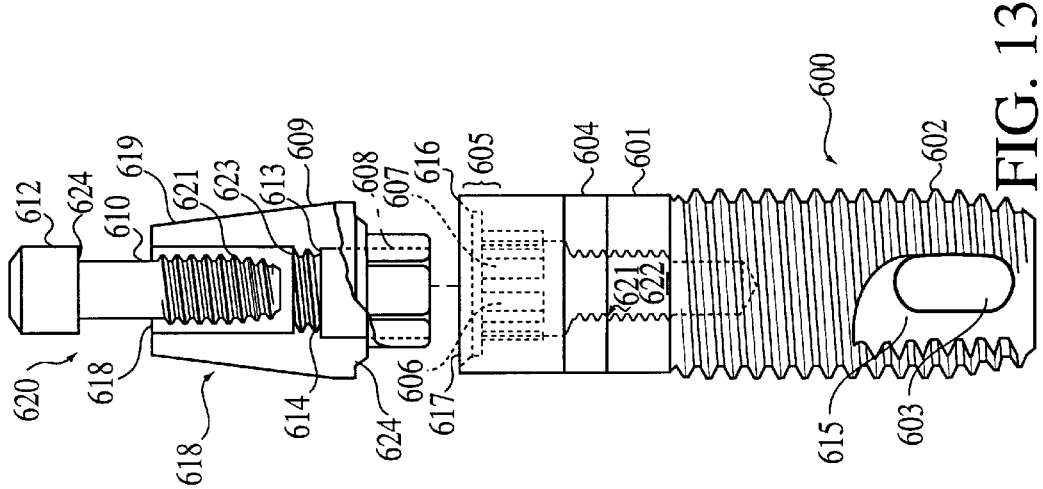
FIGS. 11–13 are side elevation views of another embodiment of a root-form, one-part endosseous dental implant having an externally-threaded body portion, a neck portion and an abutment portion that includes a peripheral, chamfered shoulder and, inside said shoulder, internal wrench-engaging surfaces that form part of an internally-threaded shaft.

FIG. 13 shows root-form, one-part endosseous dental implant 600 having externally-threaded body portion 602, through-hole 603 that passes through self-tapping cutter region 615. Above externally-threaded body portion 602 is neck portion 601/604. Atop neck portion 601/604 is abutment portion 605 that forms a shoulder including flat upper surface 616 and internally-chamfered, downwardly-extending, internal surface 617. Two-part abutment extender 618 includes first part 619 having downwardly-projecting, multi-sided projection 608 that fits into and engages, anti-rotationally, the flat surfaces of multi-sided, internal wrench-engaging surfaces 607/606. Longitudinal passage 618 through abutment extender 619 receives extender screw 612. Extender screw 612 includes threaded shank 611 that passes through internally-threaded portion 614 and engages internal threads 621 in internally-threaded passage 622 inside implant 600. Cap member 612 on screw 620 includes bottom surface 624 that engages surface 623 inside passage 618 to hold abutment extender part 619 firmly atop implant 600. Extender 619 includes, around projection 608, chamfered surface 624 that fits within chamfered surface 617 atop implant 600, forming sealing engagement with implant 600.

Figure 16:
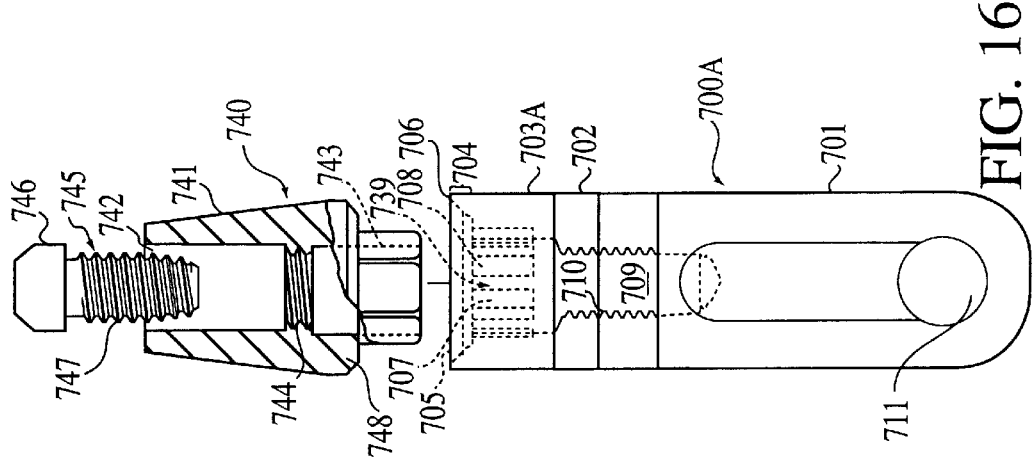
FIGS. 14–16 are side elevation views of another embodiment of a root-form, one-part endosseous dental implant having an externally-unthreaded body portion, a neck portion, and an abutment portion that includes a peripheral shoulder and, inside said shoulder, internal wrench-engaging surfaces forming part of an internally-threaded shaft.
Figure 15:
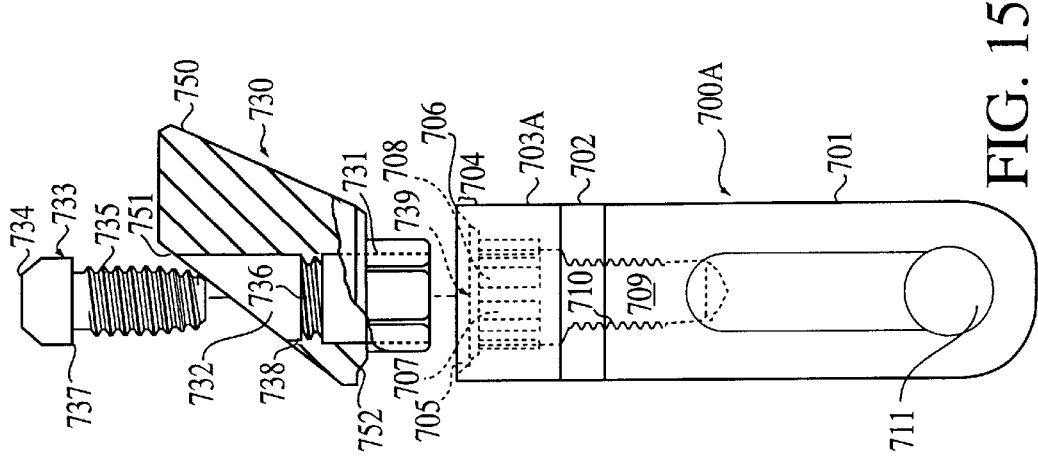
Figure 14:
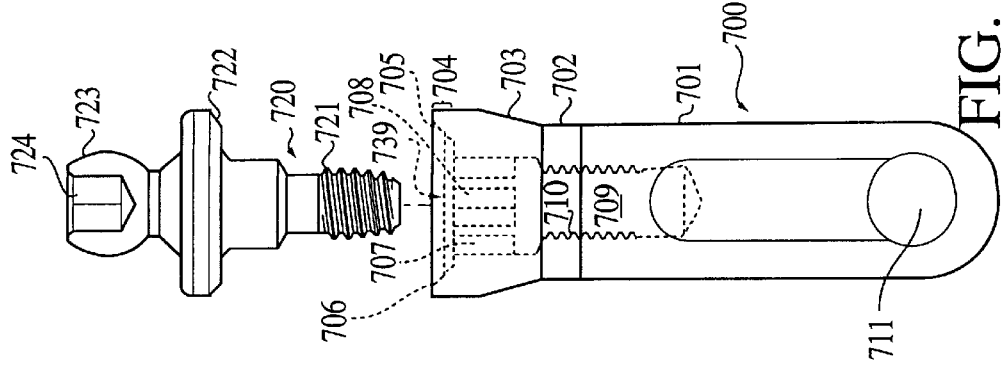

FIGS. 14, 15 and 16 show root-form, one-part endosseous dental implants 700 and 700A. Each of these implants include unthreaded, cylindrical body portion 701 with through-hole 711 forming near the apical end of the implant. Each of these implants included internally-threaded shaft 709 with internal threads 710. Each of these implants includes neck portion 702. The implant shown in FIG. 14 also includes neck portion 703 that flares outwardly. The implants in FIGS. 1 5 and 16 include neck portion 703A that is substantially the same in diameter as neck portion 702. Each of the implants also includes abutment portion 704 that includes in flat upper surface 706 on a shoulder formed, in part, by internally-chamfered, downwardly-extending surface 705. Internal wrench-engaging surfaces 707/708 are part of internally-threaded shaft 709.

The implant of FIG. 14 is shown with one-part abutment extender 720. Extender 720 includes threaded shank 721, sealing surface 722, and upward projection 723 with internal wrench-engaging surfaces 724. Abutment extender 720 screws into internal threads 710 with surface 722 seating on surface 705 to form sealing engagement between extender 720 and implant 700.

In FIG. 15, implant 700A is shown for use with abutment extender 730. Abutment extender 730 includes tapered sidewall surfaces 750/751 and internal longitudinal passage 732. Passage 723 receives abutment extender screw 733 with its threaded shank 735 and cap member 734. Cap member 734 includes flat bottom surface 737 that engages flat surface 738 to hold abutment extender 730 firmly to implant 700A. Chamfered surface 752 is complementary in size and shape to internally-chamfered surface 705 and seats firmly and sealingly in surface 705 when abutment extender 730 is in place atop implant 700A, as FIG. 15 shows. Multi-sided projection 731 fits into internal wrench-engaging surfaces 707/708 of implant 700A to prevent rotation of the abutment extender with respect to implant 700A.

FIG. 16 shows abutment 700A used with abutment extender 740. Abutment extender 740 includes inwardly-tapered external surface 741 and multi-sided projection 743 that engages flat internal wrench-engaging surfaces 707/708. Extender 740 includes internally-threaded passageway 744 through which threaded shank 747 of abutment screw 745 passes. Cap member 746 on screw 745 engages the surfaces surrounding the opening to threaded passage 744 when the threads of shank 742 engage internal threads 710 in internally-threaded passage 709. Chamfered surface 748 on extender 740 seats firmly in internally-chamfered surface 707 of abutment portion 704.

Figure 19:
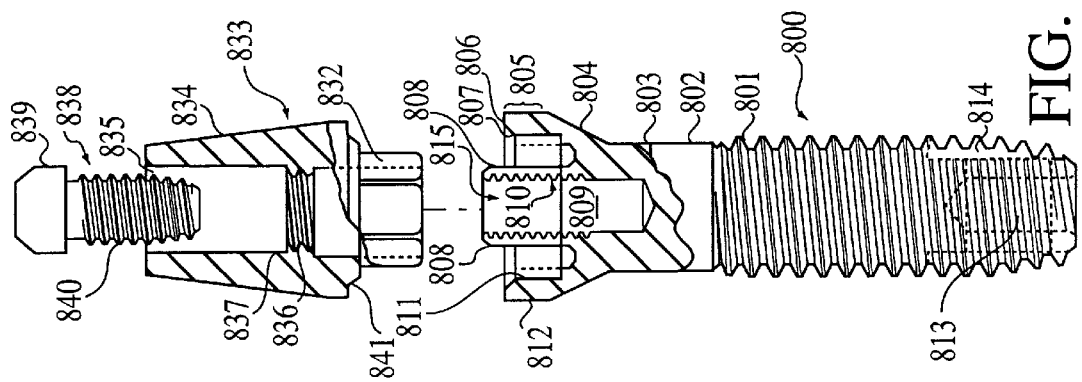
FIGS. 17–19 are side elevation views of another embodiment of a root-form, one-part endosseous dental implant having an externally-threaded body portion, a neck portion, and an abutment portion that includes a peripheral shoulder and, inside said shoulder, wrench-engaging surfaces formed on the internal wall surface of the shoulder, and an upwardly-extending, substantially cylindrical projection that includes an opening into an internally-threaded shaft.
Figure 18:
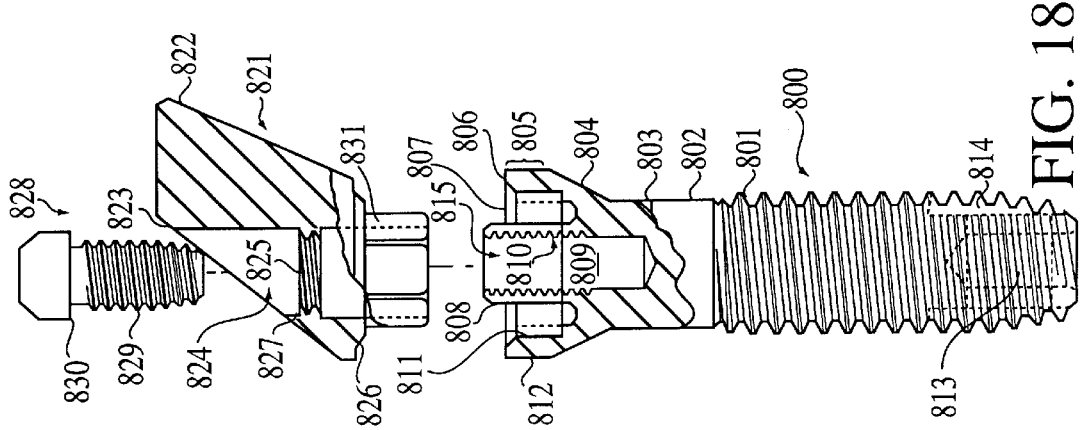
Figure 17:
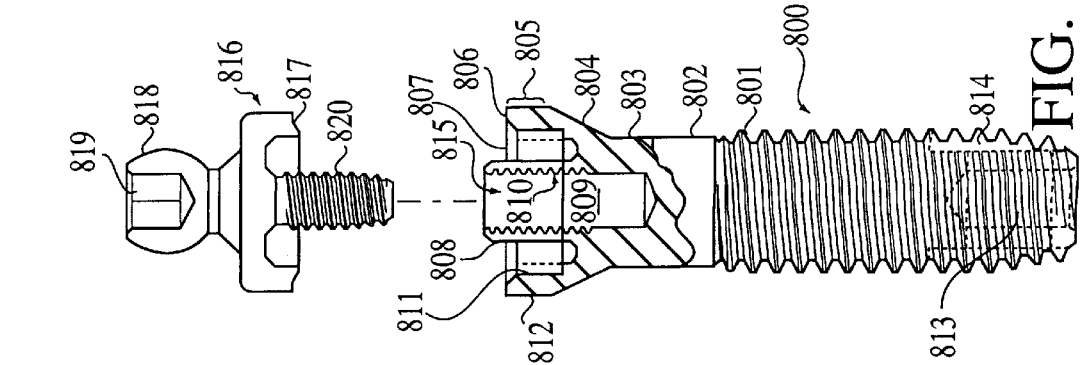

FIGS. 17, 18 and 19 show root-form, one-part endosseous dental implant 800 having externally-threaded body portion 801 that includes, near its distal end, apical longitudinal opening 813 and self-tapping cutter 814. Atop body portion 800 is cylindrical neck portion 802/803 and outwardly-flaring neck portion 804. Above neck portion 802/803/804 is abutment portion 805 formed by external shoulder 812. Shoulder 812 has flat surface 806 at the top and internally-chamfered region 807 formed at the internal edge of flat surface 806. Shoulder 812 surrounds a hole within which substantially cylindrical, externally-unthreaded projection 808 extends upwardly and above flat surface 806. At the top of projection 808 is opening 815 to internally-threaded passage 809 having internal threads 810. Projection 808 projects above upper surface 806 a distance sufficient to permit interconnection of a plurality of these implants placed in diverging, non-parallel sites in a common jawbone.

In FIG. 17, abutment 800 is shown for use with abutment extender 816. Extender 816 includes threaded shank 820 that engages internal threads 810 in internally-threaded passage 809 of implant 800. With extender 816 seated atop implant 800, chamfered surface 817 at the edge of extender 816 seats on flat surface 806 and internally-chamfered surface 807 of implant 800. Extender 817 includes ball connector 818 with internal wrench-engaging surfaces 819.

In FIG. 18, implant 800 is shown for use with abutment extender 821. Extender 821 includes upwardly-tapered surfaces 822/823 and downwardly-projecting, multi-sided projection 831 that fits into internal, multi-sided, wrench-engaging surface 811 formed on the inner wall of shoulder 812. Projection 831 and inner wall surface 811 have the same number of contiguous flat surfaces and engage one another anti-rotationally with extender 821 seated on implant 800.

Extender 821 is held to implant 800 with screw 828 that includes threaded shank 829 and cap portion 830. Threaded portion 829 screws through internal threaded portion 825 and internal passage 824 of extender 821. The bottom of cap portion 830 seats on surface 827 inside extender 821, holding extender 821 firmly atop implant 800. With extender 821 seated atop implant 800, chamfered surface 826 seats firmly on chamfered surface 807 of implant 800.

FIG. 19 shows implant 800 used with abutment extender 833. Extender 833 includes upwardly-inwardly-tapering surface 834 and downwardly-projecting, multi-sided projection 832. Projection 832 includes the same number of contiguous flat surfaces as on wrench-engaging surface 811, formed on the inner wall surface of shoulder 812. Thus, extender 834 seats anti-rotationally by engagement of multi-sided projection 832 with multi-sided surface 811 on implant 800. Extender 833 is held to implant 800 with screw 838 that includes threaded shank 840 and cap portion 839. Threaded portion 840 screws through internal threaded portion 836 in longitudinal passage 835 and extender 833. Bottom surface of cap portion 839 seats on surface 837, holding extender 833 firmly on implant 800. With extender 833 seated atop implant 800, chamfered surface 841 seats on flat surface 806 and chamfered surface 807 to form sealing engagement between implant 800 and extender 833.

Figure 22:
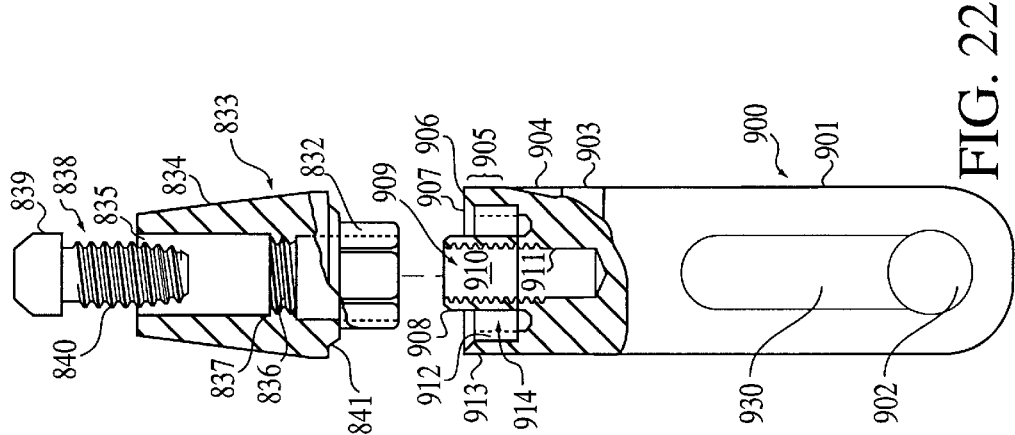
FIGS. 20–22 are side elevation views of another embodiment of a root-form, one-part endosseous dental implant having an externally-threaded body portion, a neck portion, and an abutment portion that includes a peripheral shoulder and, inside said shoulder, wrench-engaging surfaces formed on the internal wall surface of the shoulder, and an upwardly-extending, substantially cylindrical projection that includes an opening into an internally-threaded shaft.
Figure 21:
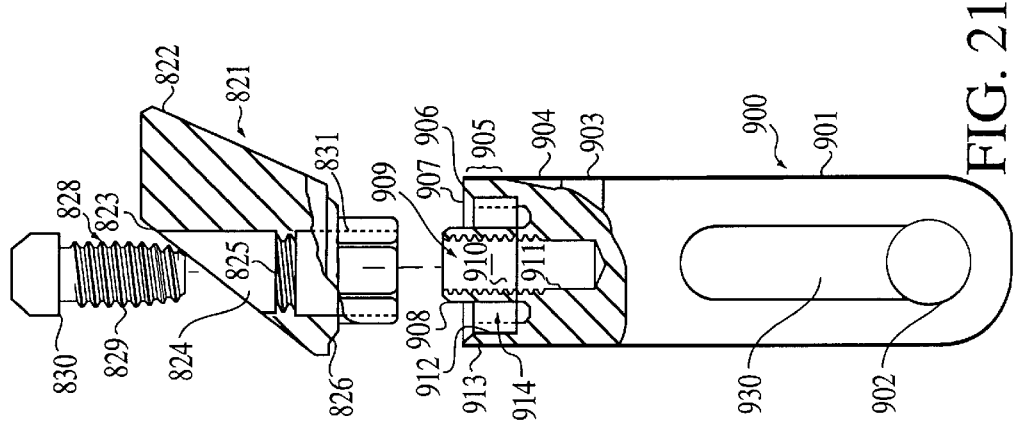
Figure 20:
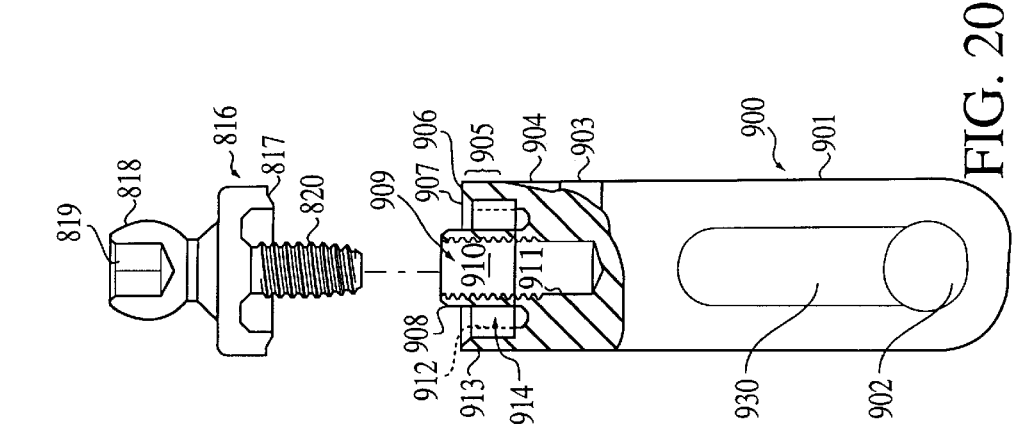

FIGS. 20, 21 and 22 each show root-form, one-part, externally-unthreaded endosseous dental implant 900 with unthreaded body portion 901 and, near the apical end of body portion 901, through-hole 902. Body portion 901 also includes longitudinal groove 930. There may be a plurality of such grooves spaced, preferably equidistantly, around the circumference of body portion 901. Atop body portion 901 are neck portions 903/904 of substantially the same diameter and circumference as body portion 901. Atop neck portion 903/904 is abutment portion 905 formed by external, cylindrical, unthreaded wall surface 913 and internal, multi-sided wall surface 912. Inside wall surface 913 is trepanned hole 914. Extending upwardly from the bottom of trepanned hole 914 is substantially cylindrical and externally-unthreaded projection 908. Projection 908 projects above flat surface 906 at the top of implant 900 and above internally-chamfered surface 907 that extends downwardly and inwardly from flat surface 906 toward projection 908. Projection 908 has, at its top, opening 909 into internally-threaded passage 910 with internal threads 911. Projection 908 extends above flat surface 906 a distance sufficient to connect, as by splinting, a plurality of these implants placed in diverging sites in a common jawbone.

The implant of FIG. 20 is shown for use with abutment extender 816. Extender 816 includes threaded shank 820 that screws into internal threads 911 of internally-threaded passage 910. With extender 816 seated firmly atop abutment 900, chamfered surface 817 mates with and forms sealing engagement with flat surface 906 and chamfered surface 907 of implant 900. Extender 816 includes ball connector 818 with internal wrench-engaging surfaces 819.

In FIG. 21, implant 900 is shown for use with abutment extender 821. Extender 821 includes downwardly-projecting, multi-sided projection 831 with the same number of contiguous flat sides as internal surface 912 of implant 900. With abutment extender 821 seated atop implant 900, surface 826 forms sealing engagement with internally-chamfered surface 906 and upper flat surface 906. Longitudinal passage 824 through extender 821 includes threaded region 825. Extender screw 828 includes threaded shank 829 and cap portion 830. When screwed into internal threads 825 of extender 821 and then into internal threads 911 of implant 900, abutment extender screw 828 holds abutment extender 821 firmly atop implant 900.

FIG. 22 shows implant 900 for use with abutment extender 833. Extender 833 includes downwardly-projecting, multi-sided projection 832 that has the same number of flat contiguous sides as internal, wrench-engaging surface 912. With extender 833 seated atop implant 900, surface 841 seats firmly against internally-chamfered surface 907 and flat surface 906 of implant 900. Extender screw 833 includes threaded shank 840 and cap portion 839. Screw 838 screws into threads 836 inside extender 833 and then into internal threads 911 of internal passage 911 through opening 909, and holds extender 833 firmly atop implant 900.

Figure 25:
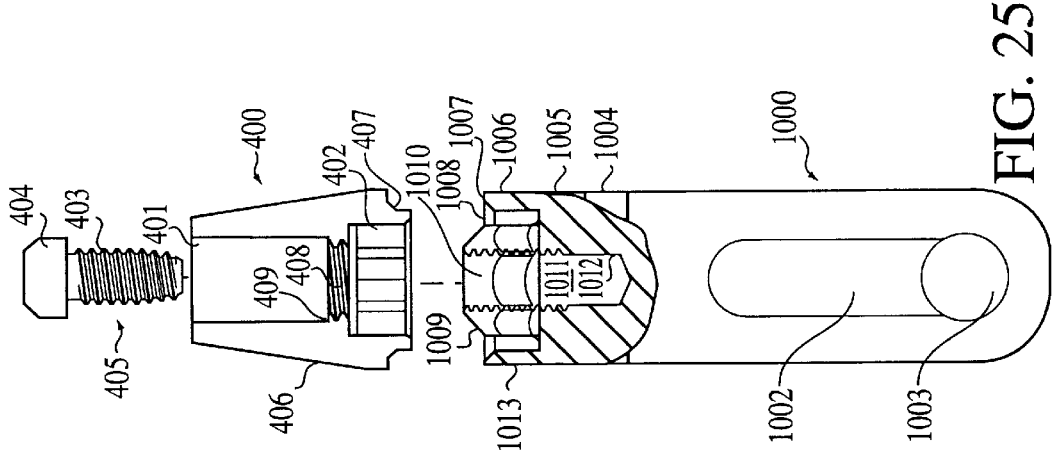
FIGS. 23–25 are side elevation views of another embodiment of a root-form, one-part endosseous dental implant having an externally-unthreaded body portion and substantially the same neck and abutment portions as the implants shown in FIGS. 3 and 4.
Figure 24:
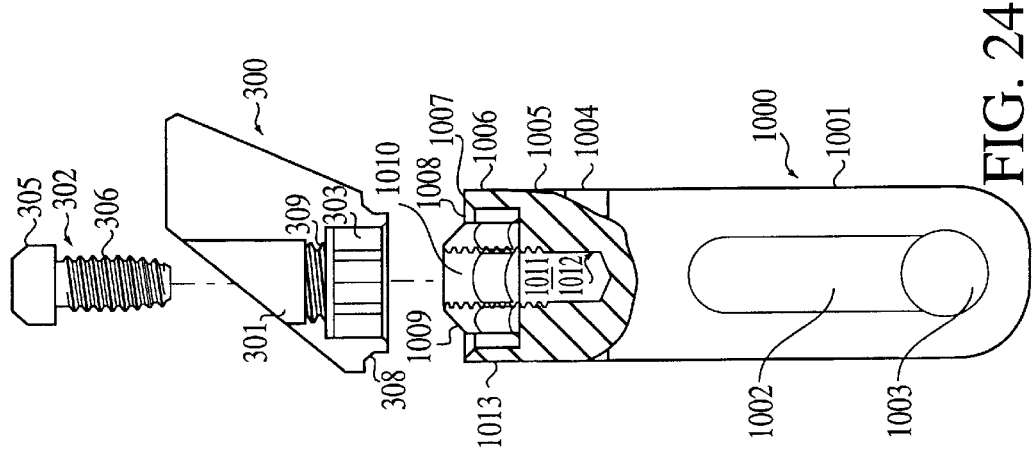
Figure 23:
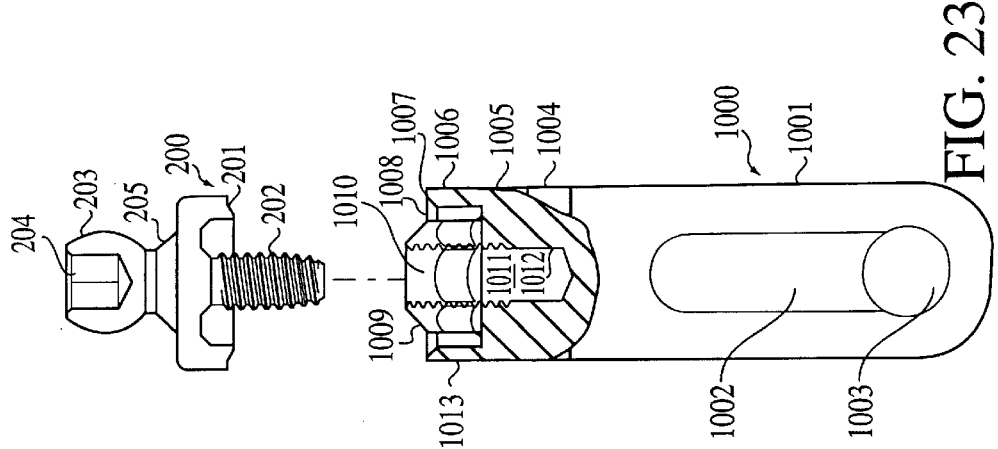

FIGS. 23, 24 and 25 show root-form, one-part endosseous dental implant 1000 with externally-unthreaded body portion 1001. Body portion 1001 includes one or more external, longitudinally-extending grooves 1002 and through-hole 1003. Atop body portion 1001 is neck portion 1004/1005. Atop neck portion 1004/1005 is abutment portion 1006. Atop abutment portion 1006 is flat surface 1007 and, extending inwardly and downwardly from surface 1007, internally-chamfered surface 1008. External, multi-sided projection 1009 projects upwardly from the hole formed by shoulder 1013. External projection 1010 is substantially the same in size, shape and dimensions as external projection 114 in FIG. 4 and projection 96 in FIG. 3.

In FIG. 23, implant 1000 is shown for use with abutment extender 200, which includes threaded shank 202 for threaded engagement with internal threads 1012 and internally-threaded passage 1011 of implant 1000. When fully seated atop implant 1000, surface 201 of extender 200 forms sealing engagement with surfaces 1007/1008 of implant 1000.

FIG. 24 shows implant 1000 for use with abutment extender 300. Extender 300 includes internal, multi-sided wrench-engaging surfaces 303 that seat themselves on complementary, multi-sided surfaces of projection 1009. Extender 300 is held firmly atop implant 1000 by screw 302. Screw 302 includes threaded shank 306 that threads through internal threads 309 and into threads 1012 of internal passage 1011. Cap member 305 seats itself on the shelf surrounding internally-threaded passage 309, holding the extender in place atop implant 1000.

In FIG. 25, implant 1000 is shown for use with abutment extender 400. Extender 400 includes the same parts and features as extender 400 shown in FIG. 10. Extender 400 includes internal, multi-sided wrench-engaging surfaces 402 that engage with the external, multi-sided surfaces of projection 1009 atop implant 1000. Extender 400 is held firmly atop implant 1000 by means of screw 405. Screw 405 includes threaded shank 406 that threads through internal threads 408 and into threads 1012 of internally-threaded passage 1011. Cap member 404 holds externally-threaded screw 405 onto surface 409 which, in turn, holds extender 400 firmly atop implant 1000. With abutment extender 400 seated atop implant 1000, chamfered surface 407 forms sealing engagement with internally-chamfered surface 1008 and upper flat surface 1007.

FIG. 26 shows root-form, one-part endosseous dental implant 1100 having externally-threaded body portion 1101, through-hole 1102 formed near the apical end of body portion 1101, in self-tapping threads. Above threaded body portion 1101 are substantially cylindrical neck portions 1103/1104, and outwardly-flared neck portion 1105. Atop neck portion 1105 is abutment portion 1106 that includes flat upper surface 1107 and inwardly-chamfered surface 1108 forming a peripheral shoulder. Inwardly-chamfered surface 1108 surrounds the opening to internally-threaded shaft 1111 that includes internal threads 1112. Internally-threaded shaft 1111 also includes, near opening 1116, splined, wrench-engaging surfaces 1109/1110.

Abutment extender 1114 includes male, splined projection 1113 that fits into and interlocks with internal splines 1109/1110. Extender 1114 is held firmly atop implant 1100 by means of screw 1115 which screws through extender 1114 and into internal threads 1112.

FIG. 28 shows a top plan view of the splined, wrench-engaging surfaces of implant 1100 as seen through opening 1116.

FIG. 27 shows root-form, one-part endosseous dental implant 1200 that includes externally-threaded body portion 1201 and through-hole 1202. Atop threaded body portion 1201 are neck portions 1203/1204 and abutment portion 1205. Abutment portion 1205 includes flat upper surface 1206 and internally-chamfered surface 1207, forming a peripheral shoulder. Inwardly-chamfered surface 1207 surrounds opening 1214 to internally-threaded shaft 1212 that includes internal threads 1213. Just below opening 1214 and inside internally-threaded shaft 1212 are splined, wrench-engaging surfaces 1208/1209. Surfaces 1208/1209 receive and engage splined projection 1211 on abutment extender 1210.

Abutment extender 1210 is held to implant 1200 by means of threaded abutment screw 1215 which screws through extender 1210 and into internal threads 1213 of implant 1200.

FIG. 29 shows root-form, one-part endosseous dental implant 1300 that includes externally-unthreaded, cylindrical body portion 1301, apical through-hole 1302 and longitudinally-extending groove 1303. Atop threaded body portion 1301 are neck portions 1304/1305. Atop neck portions 1304/1305 is abutment portion 1306 that includes flat upper surface 1307 and inwardly-extending, chamfered surface 1308 forming a shoulder portion. Surface 1308 surrounds opening 1316 into internally-threaded shaft 1311 that includes internal threads 1312. Just inside and below opening 1316 are splined, internal, wrench-engaging surfaces 1309/1310. Abutment extender 1313 includes splined projection 1314 that fits into and interlocks with splined internal wrench-engaging surfaces 1309/1310.

Abutment extender 1313 is held to implant 1300 by means of extender screw 1313 which screws through the internal threads of extender 1313 and into internal threads 1312 of implant 1300.

Figure 30:
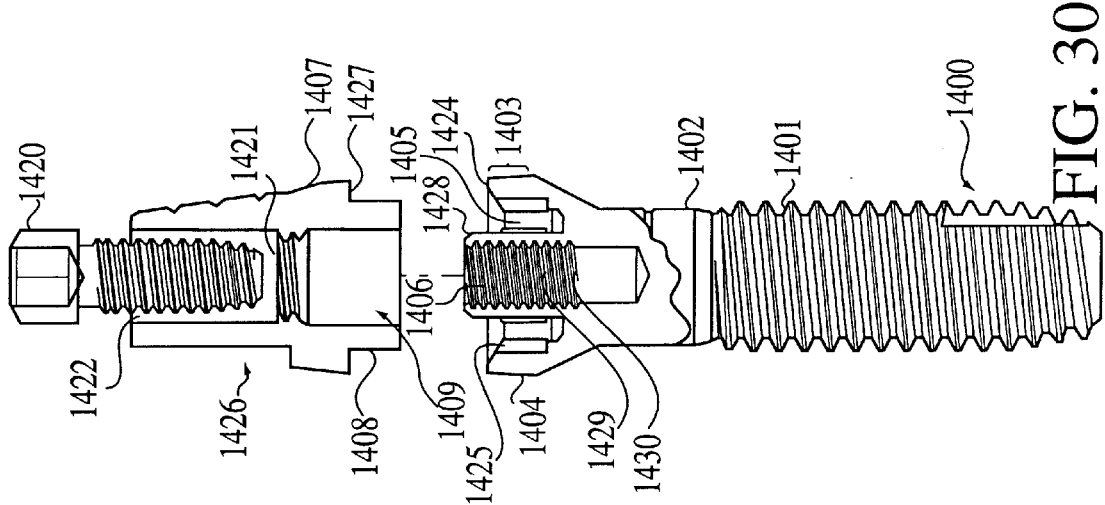
FIG. 30 shows a side elevation view of another embodiment of a root-form, one-part endosseous dental implant having an externally-threaded body portion, a neck portion, and a downwardly, outwardly tapering abutment portion that includes a peripheral shoulder and, inside said shoulder, wrench-engaging surfaces formed on the internal wall surface of the shoulder, and, an upwardly-extending, substantially cylindrical projection that includes an opening into an internally-threaded shaft, shown for use with an abutment extender that has a complementary, tapered mating portion that fits atop the abutment portion of the implant.

FIG. 30 shows a side elevation view of root-form, one-part endosseous dental implant 1400 having externally-threaded body portion 1401. Implant 1400 includes upwardly extending projection 1406 with an opening leading to internally-threaded shaft 1429 that includes internal threads 1430. Above externally-threaded body portion 1401 are neck portion 1402 and abutment portion 1403. Abutment portion 1403 includes flat upper surface 1424 and internal wall surface 1425 and external wall surface 1404. Wall surface 1425 includes multi-sided, wrench-engaging surfaces. Surface 1404 tapers outwardly and downwardly from flat surface 1424 at an angle of approximately 8 degrees with respect to the plane in which surface 1424 lies.

FIG. 30 shows implant 1400 used with abutment extender 1426. Extender 1426 includes outwardly, downwardly tapering external surface 1407 terminating at ledge portion 1427. Extender end portion 1408 is cylindrical in shape, may taper inwardly and downwardly, if desired, to form a friction fit with wall surface 1425, and has a size and shape sufficient to fit into the trepanned hole formed between upwardly extending projection 1428 and internal wall surface 1425. Extender 1426 includes cavity 1409 that has a size and shape sufficient to fit over projection 1428.

Figure 31:
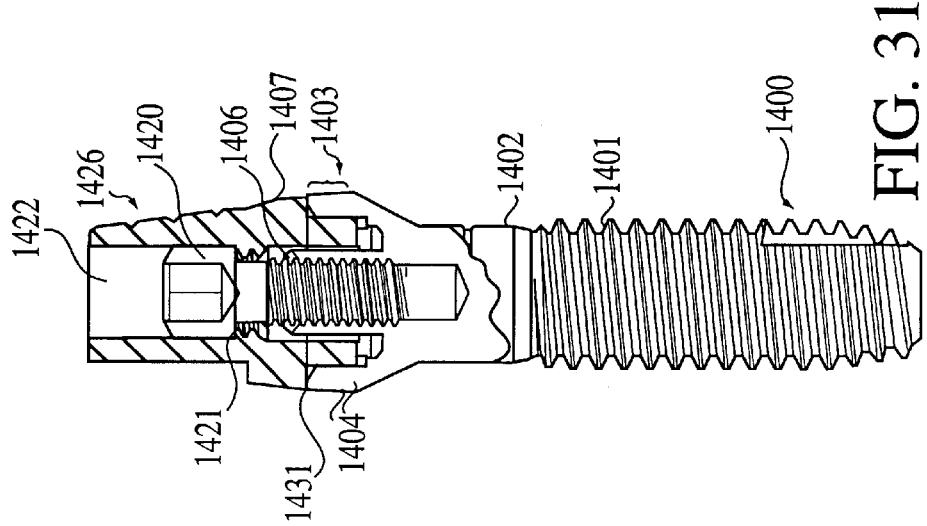
FIG. 31 shows a side elevation view of the implant and abutment extender shown in FIG. 30, with the abutment extender shown in FIG. 30 fitted in place atop the implant.

As FIG. 31 shows, with extender 1426 fitted into the trepanned hole between projection 1428 and internal wall surface 1425, abutment extender surface 1407 mates with and forms a flush, continuous surface with downwardly, outwardly tapering external wall surface 1404. Abutment extender screw 1420 screws through internal threads 1421 in extender 1426, and into internal threads 1430 in internally-threaded shaft 1429 to hold extender 1426 in place atop implant 1400.

The combination of implant 1400 with abutment extender 1426, as shown in FIG. 31, permits attachment of a prosthesis, e.g. a false tooth, that extends below juncture line 1431 between extender 1426 and implant 1400. As a result, the prosthesis extends below mucosal tissue atop the implant, producing a natural profile to the restoration, and an aesthetically-pleasing appearance upon restoration. For example, a false tooth may be formed from the bottom of external wall surface 1404, covering and protecting juncture line 1431.

Figure 32:
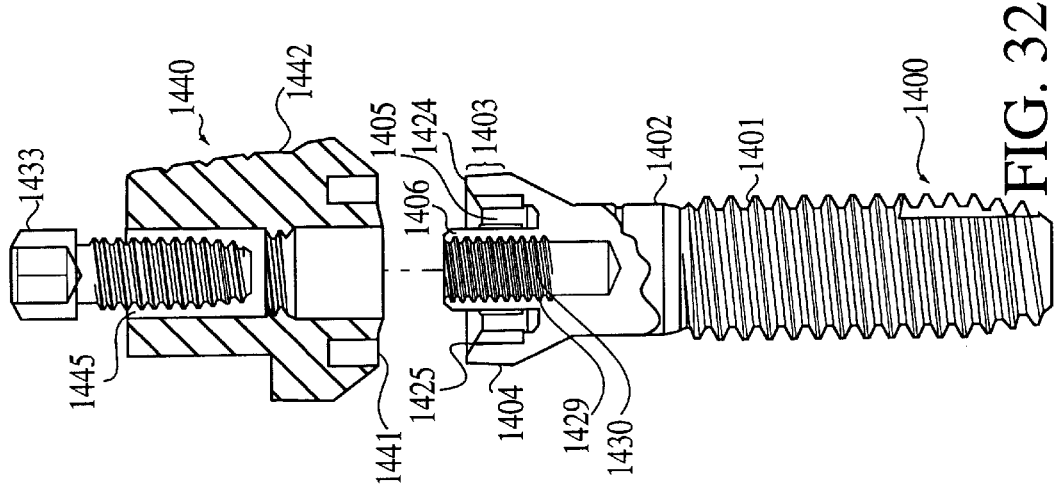
FIG. 32 shows a side elevation view of another embodiment of a root-form, one-part endosseous dental implant shown in FIG. 30, here shown for use with an abutment extender that includes an end portion that fits over the outwardly, downwardly tapering external wall of the abutment portion.

FIG. 32 shows the same root-form, one-part endosseous dental implant 1400 shown in FIGS. 30 and 31. As in FIGS. 30 and 31, implant 1400 includes abutment portion 1403. Abutment portion 1403 includes flat upper surface 1424, internal wall surface 1425 with multi-sided, wrench-engaging surfaces, and external wall surface 1404. Surface 1404 tapers outwardly and downwardly from flat surface 1424 at an angle of approximately 8 degrees with respect to the plane in which surface 1424 lies.

FIG. 32 shows implant 1400 used with implant extender 1440. Extender 1440 includes body portion 1442, central longitudinal opening 1445, internally-threaded region 1444, and, at its bottom end, annular cavity 1441.

Figure 33:
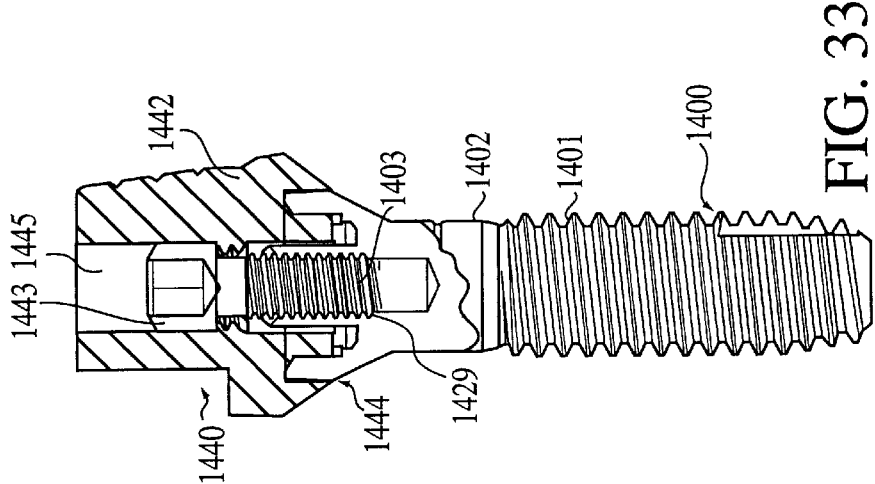
FIG. 33 shows a side elevation view of the implant and abutment extender shown in FIG. 32, with the abutment extender shown in FIG. 32 fitted into place atop the abutment portion of the implant.

As FIG. 33 shows, with abutment extender 1440 fitted atop implant 1400, abutment portion 1403 fits into annular cavity 1441 which overlies external wall surface 1404. Abutment extender screw 1443 threads through internally-threaded region 1444 of abutment extender 1440 and into internal threads 1430 in internally-threaded shaft 1429 to hold abutment extender 1440 firmly atop implant 1400. Since abutment extender 1440 is of sufficient size to fit over the peripheral shoulder formed by external wall 1404, internal wall 1425 and upper surface 1424 atop implant 1400, extender 1440 can be trimmed to better accommodate angulation and parallelism requirements for prostheses to be attached to the combination of implant 1400 and extender 1440. The size and shape of extender 1444 is adequate to create a natural profile in a wide tooth restoration such as a molar.

What is claimed is:

1. A one-part, endosseous, root-form dental implant including:

a body portion for insertion into an opening in the jawbone of a patient;

a neck portion formed above said body portion, said neck portion projecting above said body portion a sufficient length to project through mucosal tissue above said jawbone opening;

an abutment portion formed above said neck portion, said abutment portion including a peripheral shoulder projecting upwardly at the top of said implant to support attachment of a connector for at least two such implants placed in non-parallel, common jawbone sites;

an internally-threaded shaft extending downwardly into said implant from the top surface of said implant;

surrounding the opening to said internally-threaded shaft, an externally-unthreaded, substantially cylindrical projection lying in a hole formed by said shoulder; and on the inner surface of said shoulder, multi-sided wrench-engaging surface.

2. The implant of claim 1 wherein the top of said abutment portion has a size and shape adapted to form a sealed margin with a prosthetic attachment.

3. The implant of claim 1 or claim 2 wherein said projection extends above the upper surface of said shoulder, and said projection tapers downwardly and outwardly from a flat upper surface to provide friction-fit connection to a female abutment extender.

4. The implant of claim 3 wherein said body portion is externally-threaded, said neck portion includes a substantially cylindrical portion contiguous with said neck portion, and an outwardly flaring portion atop said substantially cylindrical portion, and said shoulder is atop said outwardly flaring portion.

5. The implant of claim 1 or claim 2 wherein said body portion is externally-threaded, said neck portion includes a substantially cylindrical portion contiguous with said neck portion, and an outwardly flaring portion atop said substantially cylindrical portion, and said shoulder is atop said outwardly flaring portion.

6. The implant of claim 1 or claim 2 wherein said wrench-engaging surfaces have from 4 to 8 flat, contiguous sides, or a plurality of splines.

7. The implant of claim 1 or claim 2 further comprising an abutment extender that has a lower surface adapted to seat on and form sealing engagement with said peripheral shoulder.

8. The implant of claim 3 further comprising an abutment extender that has a lower surface adapted to seat on and form a sealing engagement with said peripheral shoulder.

* * * * *